(12) United States Patent
Shinozuka et al.

(10) Patent No.: US 8,157,811 B2
(45) Date of Patent: Apr. 17, 2012

(54) TREATMENT DEVICE FOR ENDOSCOPE

(75) Inventors: Minoru Shinozuka, Hachioji (JP);
Ichiro Takahashi, Sagamihara (JP);
Tomihisa Kato, Nagoya (JP);
Munechika Matsumoto, Nagoya (JP)

(73) Assignees: Olympus Corporation, Tokyo (JP);
Asahi Intecc Co., Ltd., Nagoya-Shi, Aichi (JP)

( * ) Notice: Subject to any disclaimer, the term of this patent is extended or adjusted under 35 U.S.C. 154(b) by 0 days.

(21) Appl. No.: 10/316,590

(22) Filed: Dec. 11, 2002

(65) Prior Publication Data
US 2003/0139750 A1    Jul. 24, 2003

Related U.S. Application Data

(63) Continuation of application No. PCT/JP02/02079, filed on Mar. 6, 2002.

(30) Foreign Application Priority Data

Apr. 12, 2001    (JP) ................................ 2001-113410

(51) Int. Cl.
*A61B 17/221*    (2006.01)
(52) U.S. Cl. ...................................................... 606/113
(58) Field of Classification Search ................. 606/103, 606/113, 127, 200, 110, 79, 106, 167, 170; 57/204, 243, 248
See application file for complete search history.

(56) References Cited

U.S. PATENT DOCUMENTS

| | | | | |
|---|---|---|---|---|
| 3,358,435 | A | * | 12/1967 | Peene ............................... 57/218 |
| 3,538,702 | A | * | 11/1970 | Wolf et al. ........................ 57/218 |
| 3,996,733 | A | * | 12/1976 | Holmes ............................ 57/212 |
| 4,633,871 | A |   | 1/1987 | Shinozuka |
| 4,781,016 | A | * | 11/1988 | Sato et al. ........................ 57/213 |
| 5,947,979 | A | * | 9/1999 | Ouchi et al. .................... 606/113 |
| 6,299,612 | B1 | * | 10/2001 | Ouchi .............................. 606/47 |

FOREIGN PATENT DOCUMENTS

| | | |
|---|---|---|
| DE | 40 38 206 A1 | 2/1992 |
| DE | 199 41 912 A1 | 4/2000 |
| GB | 2 321 192 A | 7/1998 |
| JP | 6-3549 * | 2/1994 |
| JP | 11-104146 | 4/1999 |
| JP | 2000-107198 | 4/2000 |
| JP | 2000-271146 | 10/2000 |
| JP | 2001-258892 | 9/2001 |
| JP | 2001-276081 | 10/2001 |
| WO | WO 92/22254 | 12/1992 |
| WO | WO 99/16363 | 4/1999 |

* cited by examiner

*Primary Examiner* — Ryan Severson
(74) *Attorney, Agent, or Firm* — Scully, Scott, Murphy & Presser, P.C.

(57) ABSTRACT

There is disclosed a treatment device for an endoscope, comprising a treatment portion in which an operation wire is forward/backward moveably inserted into a main tube of an elongated flexible tube to be inserted into a body, a tip end of the operation wire forms a loop for treatment by itself in a projection state from the main tube, and the loop is adapted to be retractable and storable in the main tube, wherein the treatment portion is formed with a wire rope obtained by integrally intertwining a plurality of side strand wires with a core strand wire, and spiral convex or concave portions continuously disposed along the outer periphery of the wire rope are formed with the side strand wires.

5 Claims, 8 Drawing Sheets

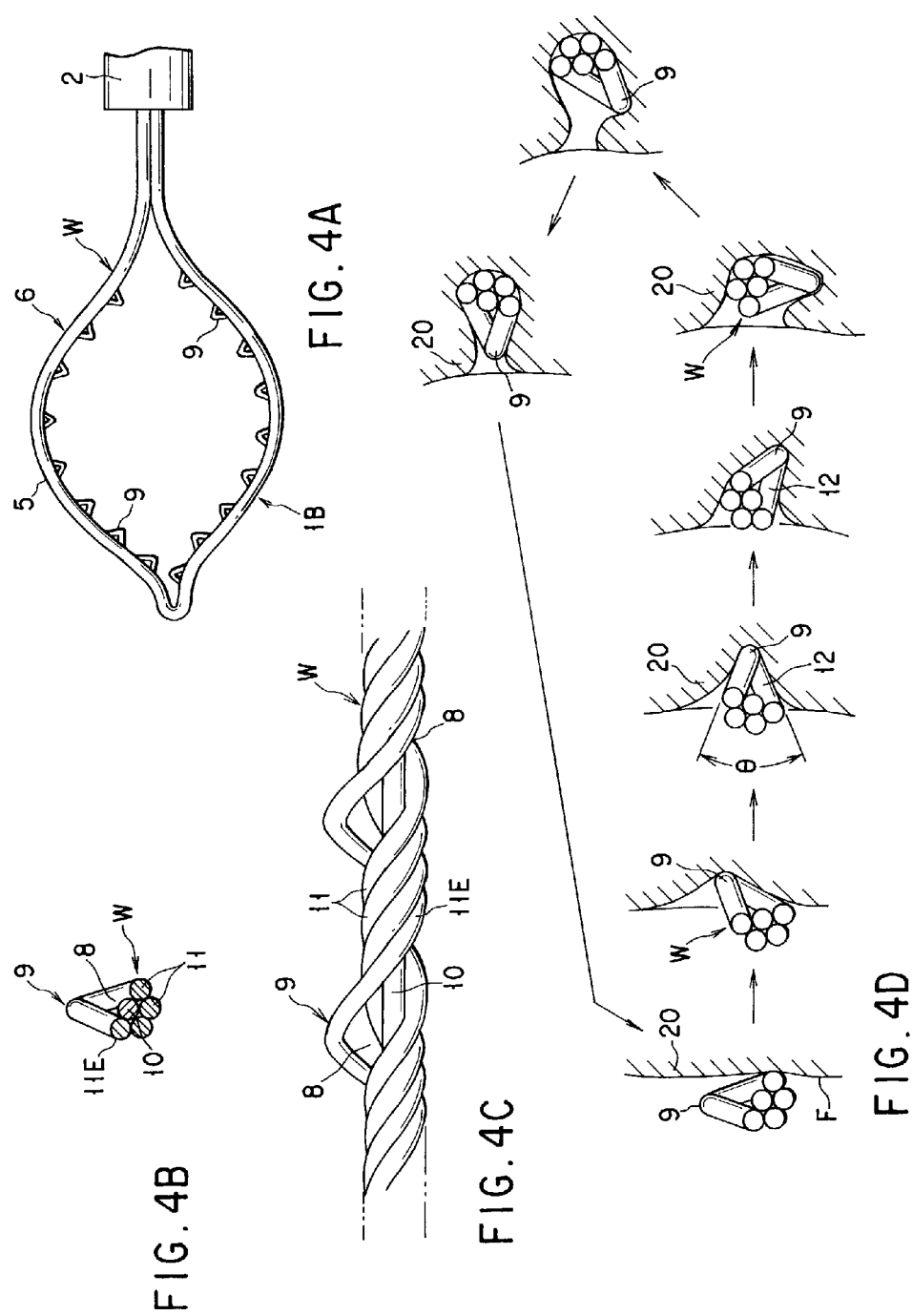

TREATMENT DEVICE FOR ENDOSCOPE

CROSS-REFERENCE TO RELATED APPLICATIONS

This is a Continuation Application of PCT Application No. PCT/JP02/02079, filed Mar. 6, 2002, which was not published under PCT Article 21(2) in English.

This application is based upon and claims the benefit of priority from the prior Japanese Patent Application No. 2001-113410, filed Apr. 12, 2001, the entire contents of which are incorporated herein by reference.

BACKGROUND OF THE INVENTION

1. Field of the Invention

The present invention relates to a treatment device for an endoscope for use in inserting the device into a body to capture and remove a polyp with a treatment portion disposed in a tip end of the device, or retaining the device in the body while capturing the polyp in the device.

2. Description of the Related Art

A treatment device for an endoscope, which captures and medically treats a polyp in a body, includes: a mode comprising: a treatment portion which projects from a tip end of a main tube to form a loop for treatment and which can freely be retracted into the main tube in a tip end of an operation wire inserted into the main tube of a flexible elongated tube to be inserted into the body. Living tissues such as a polyp are captured and fastened by the loop of the treatment portion, and thereafter the loop is retracted into the main tube so that the captured polyp is removed/treated.

However, since the polyp to be captured is a soft elastic member encapsulated in a body fluid small in contact angle and having a high-viscosity wet state, it is difficult to retain/capture the polyp by the loop for treatment. As known examples which solve this disadvantage, there are a structure in which an engagement needle is embedded in a rope material of the treatment portion, and a needle tip projects inside a loop to pierce and engage with the polyp (Jpn. Pat. Appln. KOKAI Publication No. 2000-271146), and a structure in which one wire of the rope material of the treatment portion is cut, and a cut end projects inside the loop to function as a capture needle of the polyp (Jpn. Pat. Appln. KOKAI Publication No. 2000-107198).

On the other hand, in Jpn. UM Appln. KOKOKU Publication No. 6-3549, a structure is disclosed in which a large number of slip stopper chips are attached later and fixed to a wire material of the loop for treatment, a tip end of each slip stopper chip projects inside the loop for treatment to form an engagement projection, and capturing properties of the polyp are enhanced.

Any capturing properties enhancement structure of the above-described known examples is a structure which allows a needle-shaped/projecting material rich in rigidity to project inside the loop. Therefore, when the loop is retracted and stored in the main tube, the needle-shaped/projecting material is superimposed and united to interfere with a treatment portion member or contact an inner periphery of the main tube, and a resistance in the retraction into the main tube increases to make an operation difficult. Moreover, a formation operation comprising: accurately determining a projection direction and fixing a large number of the above-described engagement needles/slip stopper chips onto the rope material of the treatment portion is laborious, requires a number of manual operations, and is inferior in processability.

Furthermore, for the above-described wire cut mode, a formation operation comprising: cutting one wire of a wire rope having a remarkably small diameter and allowing the wire to project in an accurate direction is remarkably laborious and bad in processability. Additionally, the wire rope is broken because of a strength drop, and a projecting posture of the engagement needle formed by bending the cut end of the wire accommodated in the tube is deformed so that engagement properties are degraded. As another disadvantage, the loop for treatment is caught by the rope material to which the loop is bonded, and cannot sufficiently be enlarged/deformed because of a self elastic force.

BRIEF SUMMARY OF THE INVENTION

An object of the present invention is to provide a treatment device for an endoscope which solves the above-described disadvantages of the conventional art.

According to a first aspect of the present invention, there is provided a treatment device for an endoscope, comprising: a treatment portion in which an operation wire is forward/backward moveably inserted into a main tube of an elongated flexible tube to be inserted into a body, a tip end of the operation wire forms a loop for treatment by itself in a projection state from the main tube, and the loop is adapted to be retractable and storable in the main tube, wherein the treatment portion is formed with a wire rope obtained by integrally intertwining a plurality of side strand wires with a core strand wire, and spiral convex or concave portions continuously disposed along an outer periphery of the wire rope are formed with the side strand wires.

Moreover, according to a second aspect of the present invention, there is provided a treatment device for an endoscope, comprising: a treatment portion in which an operation wire is forward/backward moveably inserted into a main tube of an elongated flexible tube to be inserted into a body, a tip end of the operation wire forms a loop for treatment by itself in a projection state from the main tube, and the loop is adapted to be retractable and storable in the main tube, wherein the treatment portion is formed with a wire rope obtained by winding a side strand wire around a core strand wire, and a wave-form portion which is formed by the core strand wire or side strand wire, projects from an outer periphery of the wire rope, and has a circular arc shape is continuously disposed in a longitudinal direction of the wire rope.

Furthermore, according to a third aspect of the present invention, there is provided a treatment device for an endoscope, comprising: a treatment portion in which an operation wire is forward/backward moveably inserted into a main tube of an elongated flexible tube to be inserted into a body, a tip end of the operation wire forms a loop for treatment by itself in a projection state from the main tube, and the loop is adapted to be retractable and storable in the main tube, wherein the treatment portion is formed with a wire rope obtained by integrally intertwining at least two strand wires having different outer diameters, and spiral convex or concave portions continuously disposed along an outer periphery of the wire rope are formed by the strand wires.

That is, the treatment device for the endoscope according to the present invention is developed from a concept in which the above-described spiral convex portion/spiral concave portion/wave-form portion disposed on the outer periphery of the wire rope constituting the loop for treatment is allowed to function as a wedge portion/bite type tool portion/fixing engagement portion for capturing/fastening a high-viscosity wet and soft living tissue. The spiral convex/concave portion is formed by means for increasing diameters of some (one to three wires) of the side strand wires of the wire rope or omitting the wires, and the wave-form portion is formed by means for drawing and raising some of the side or core strand wires out to the outer periphery of the wire rope.

The loop for treatment of the treatment device for the endoscope according to the present invention constituted as described above is retained onto living tissues such as a polyp, narrowed down, and fastened. Therefore, the inside of the wire rope of the loop for treatment and the surface of the living tissue slip with respect to each other and contact each other with friction in a relation. A surface one point of the living tissue is brought into contact with the successively and dynamically displaced spiral convex portion/spiral concave portion/wave-form portion existing in the wire rope, and narrowed/fastened in a process.

Therefore, the loop for treatment including the spiral convex portion/wave-form portion functions as the bite type tool portion or fixing engagement portion which acts as a wedge to relatively easily bite into the living tissue in a point of a vertex of the convex portion/wave-form portion disposed opposite to the living tissue, moves with respect to the tissue, removes a viscous material from the surface, and effectively bites into the living tissue. Therefore, the loop for treatment can effectively capture/fasten the living tissue.

Moreover, for the loop including the spiral concave portion, the spiral concave portion receives the living tissue, moves with respect to the living tissue, and bites into the tissue. Moreover, the spiral concave portion functions as a drain ditch of the viscous material on the living tissue surface, and similarly functions as the remarkably effective bite type tool portion or fixing engagement portion, so that the loop for treatment can effectively capture/fasten the living tissue.

For details, since the spiral concave portion functions as the drain ditch of the viscous material of the living tissue surface, the viscous material reduces the body fluid of the living tissue surface in the wet state. This produces an effect that a mutual contact of the loop for treatment with the surface of the living tissue is brought close to a direct mutual contact of solids having a large contact angle to increase a friction coefficient. There is a peculiar effect that further enhancement of the above-described capturing/fastening action by the loop for treatment is boosted.

Moreover, when the wire rope of the treatment portion is retracted and stored in the main tube, the spiral convex portion/wave-form portion existing in the outer periphery interferes with the main tube inner periphery or the folded/superimposed wire rope outer periphery. However, the convex portion vertex has a circular arc shape and a small interference resistance. Therefore, without especially increasing a retraction resistance, the wire rope can smoothly be retracted and stored in the main tube. Moreover, there is no fear that the main tube or wire rope is damaged, and the loop formation of the treatment portion and retraction/containment can smoothly and continuously be repeated.

Furthermore, the above-described spiral convex portion/ spiral concave portion/wave-form portion is formed of the side or core strand wire of the wire rope, and therefore the forming/processing of the treatment portion can remarkably be facilitated as compared with the structure in which separate materials such as the engagement needle/engagement member including the conventional structure are attached later.

BRIEF DESCRIPTION OF THE SEVERAL VIEWS OF THE DRAWING

FIG. 1A is a front view of a treatment portion, FIG. 1B is a sectional view of a wire rope of a loop for treatment, FIG. 1C is a front view of the wire rope of the loop for treatment, and FIG. 1D is an action explanatory view of the loop for treatment.

FIG. 2A is a sectional view of the wire rope of the loop for treatment, FIG. 2B is a front view of the wire rope of the loop for treatment, and FIG. 2C is an action explanatory view of the loop for treatment.

FIG. 3A is a sectional view of the wire rope of the loop for treatment, FIG. 3B is a front view of the wire rope of the loop for treatment, and FIG. 3C is an action explanatory view of the loop for treatment.

FIGS. 4A to 4D show the treatment device for the endoscope according to one embodiment of a second aspect of the present invention, FIG. 4A is a front view of the treatment portion, FIG. 4B is a sectional view of the wire rope of the loop for treatment, FIG. 4C is a front view of the wire rope of the loop for treatment, and FIG. 4D is an action explanatory view of the loop for treatment.

FIG. 5A is a front view of the wire rope, FIG. 5B is a sectional view of the wire rope, and FIG. 5C is a front view of a side strand wire of the wire rope in a straight state.

FIGS. 6A to 6C are all sectional views of the wire rope.

FIG. 7A is a front view of the rope, FIG. 7B is a sectional view of the rope, and FIG. 7C is an action explanatory view of the rope.

FIGS. 8A, 8C are front views of the treatment portion, and FIG. 8B is a usage explanatory view of FIG. 8A.

FIG. 10A is a sectional view of the wire rope of the present invention in the embodiment shown in FIG. 9, FIG. 10B is a sectional view of the wire rope of the present invention in the embodiment shown in FIG. 1, and FIG. 10C is a sectional view of the wire rope of the present invention in the embodiment shown in FIG. 2.

DETAILED DESCRIPTION OF THE INVENTION

Figure 1B:
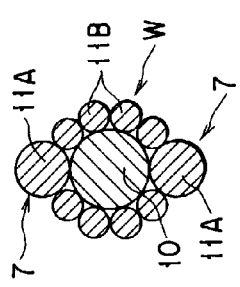
FIGS. 1A to 1D show a treatment device for an endoscope according to one embodiment of a first aspect of the present invention.
Figure 1A:
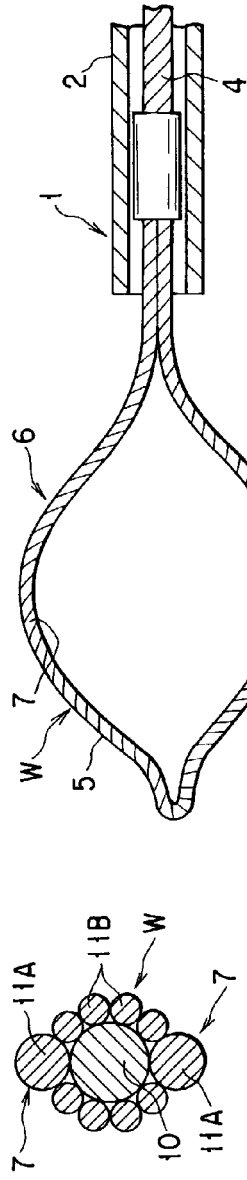
Figure 1C:
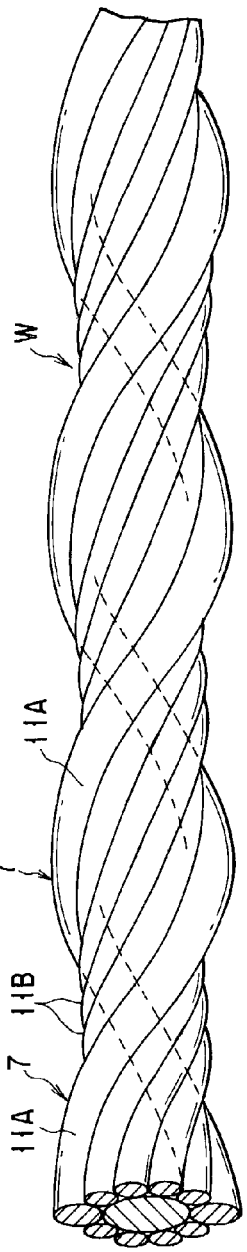
Figure 1D:
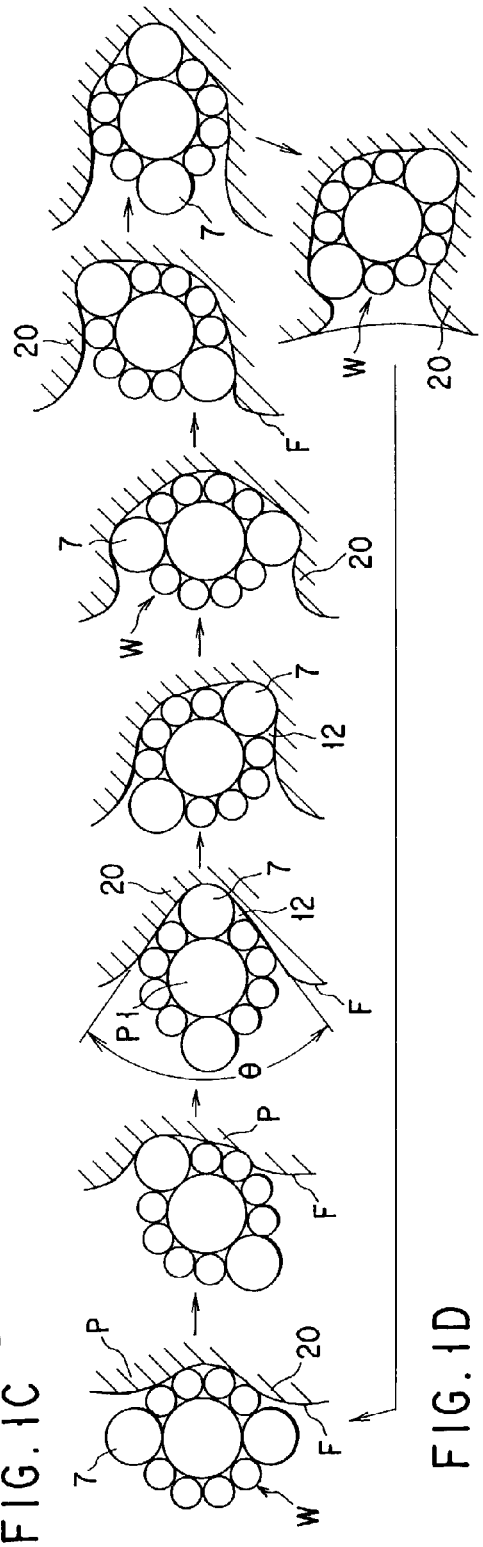

First, one embodiment of a treatment device for an endoscope according to a first aspect of the present invention will be described with reference to FIGS. 1A to 1D. That is, in a treatment device for an endoscope 1 including a treatment portion 6 in which an operation wire 4 is inserted into a main tube 2 of a flexible elongated tube member so as to be forward/backward movable, a loop for treatment 5 (hereinafter referred to simply as the loop 5) by a self elastic force in a projection state from a tip end of the main tube 2 is formed in a tip end of the operation wire 4, and elasticity of the loop 5 can be eliminated to retract/contain the loop into the main tube 2 by a pulling operation of the operation wire 4, the treatment portion 6 of the embodiment has the following constitution.

For details (see FIGS. 1B, 1C), the treatment portion 6 includes a wire rope W formed by winding a side strand wire 11 including ten round wires around a core strand wire 10 of the round wire. The ten side strand wires 11 include a combination of two large-diameter side strand wires 11A on one diameter of the core strand wire 10, and four small-diameter side strand wires 11B disposed between the large-diameter side strand wires 11A. There is provided a structure in which the large-diameter side strand wire 11A forms a spiral convex portion 7 continuously appearing on the outer periphery of the wire rope W, and the wire rope W forms the whole shape of the treatment portion 6. It is to be noted that for a size of the wire rope W of this embodiment, the diameter of the core strand wire 10=0.22 mm, the diameter of the side strand wire 11A=0.14 mm, and the diameter of the side strand wire 11B=0.07 mm.

The treatment device for the endoscope 1 including the treatment portion 6 structured as described above has the above-described action, and a living tissue 20 such as a polyp as a soft elastic body having a high-viscosity surface can remarkably effectively be captured/fastened by the loop 5. That is (see FIG. 1D), the spiral convex portion 7 of the loop 5 is wound/turned around the inner and outer peripheries of the loop 5 to repeat various changes as shown, and is disposed opposite to and in contact with a surface F of the living tissue 20. The loop 5 is drawn/shaped and the wire rope W is slid with respect to the surface F to capture/fasten the living tissue 20 in a process.

Therefore, the wire rope W of a vicinity point Pi in which a vertex of the spiral convex portion 7 is disposed opposite to the surface F of the living tissue 20 actions like a wedge by a small bite angle θ, and first bites into and fixedly engages with the surface is F. Moreover, the wire rope supports the biting engagement with the surface F of another point in which a relative posture of the surface F and spiral convex portion 7 differs, and captures/engages with the living tissue 20 so as to prevent the tissue from being easily detached.

Moreover, in a fastening process following the capture, in one point P of the surface F, as shown by an arrow, a fastening mode is achieved in which the spiral convex portion 7 is slid/dislocated with respect to the surface F and successively bites into the living tissue 20. A function of the above-described bite type tool portion or fixing engagement portion is fulfilled, and the fastening/cutting of the living tissue 20 by the loop 5 can accurately and easily be performed.

Furthermore, when the loop 5 is retracted and stored in the main tube 2, the vertex of the circular arc shape of the spiral convex portion 7 only interferes with the wire rope W, and mutual interference of the spiral convex portions 7 does not occur (two folded/superimposed spiral convex portions 7 of the wire rope W have the same inclination direction and therefore the mutual interference can be avoided). Therefore, the loop can smoothly be retracted and stored in the main tube 2.

Another embodiment of the treatment device for the endoscope 1 according to a first aspect of the present invention will next be described with reference to FIGS. 2A to 2C and 3A to 3C. That is, in the loop 5 including the wire rope W formed by winding a plurality of side strand wires 11 around the core strand wire 10, in an embodiment shown in FIGS. 2A to 2C, one (shown by a dotted line) of the side strand wires 11 is omitted in winding the wires, an empty space by the omission appears outside the wire rope W to form a continuous spiral concave portion 8, and the wire rope W including the spiral concave portion 8 constitutes the treatment portion 6.

Figure 2A:
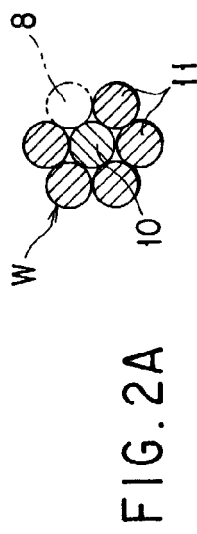
FIGS. 2A to 2C show the treatment device for the endoscope according to another embodiment of the first aspect of the present invention.
Figure 2B:
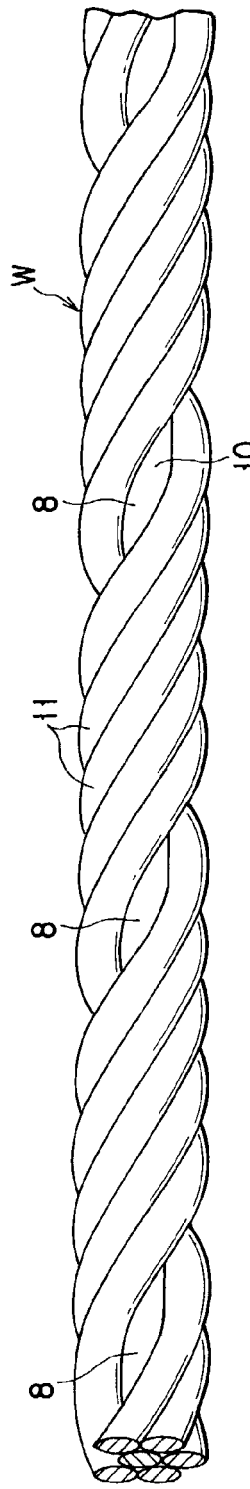
Figure 2C:
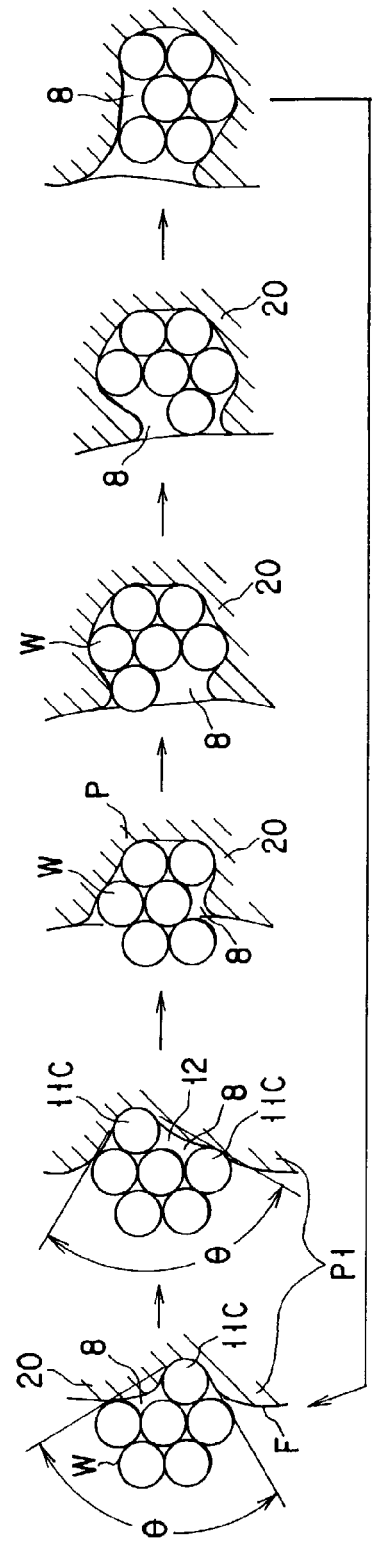

The embodiment shown in FIGS. 2A to 2C (see FIG. 2C) provides a mode in which similarly as the embodiment shown in FIG. 1, the outer periphery of the wire rope W is slid with respect to the surface F of the living tissue 20 and the relative posture of the spiral concave portion 8 and surface F is successively changed in order to capture/fasten the living tissue 20. Therefore, in a shown P1 position in which the spiral concave portion 8 is brought in the vicinity of the surface F, the wire rope W actions like the wedge by the small bite angle θ. Moreover, side strand wires 11C disposed on the opposite sides of the spiral concave portion 8 are allowed to function as the bite type tool portions, while the living tissue 20 is received, fixed, and engaged with respect to the spiral concave portion 8. Furthermore, since the spiral concave portion 8 is allowed to function as a drain ditch 12 of the viscous material in the surface F, the above-described peculiar action is performed and the capturing/fastening of the living tissue 20 can remarkably smoothly and accurately be performed.

Figure 3A:
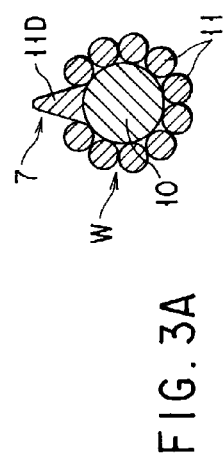
FIGS. 3A to 3C show the treatment device for the endoscope according to another embodiment of the first aspect of the present invention.
Figure 3B:
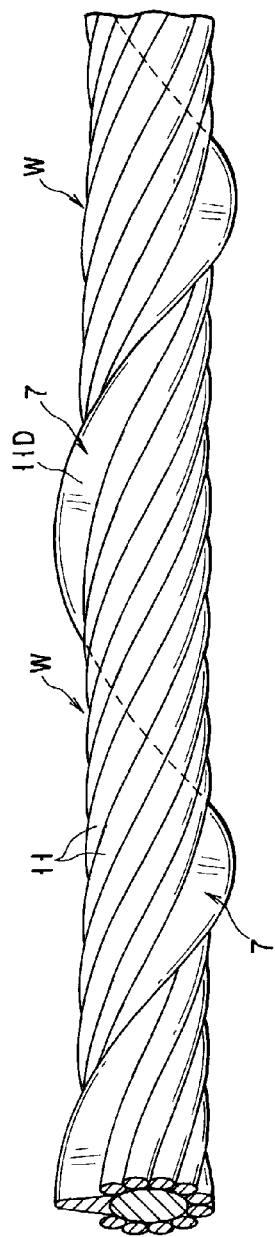
Figure 3C:
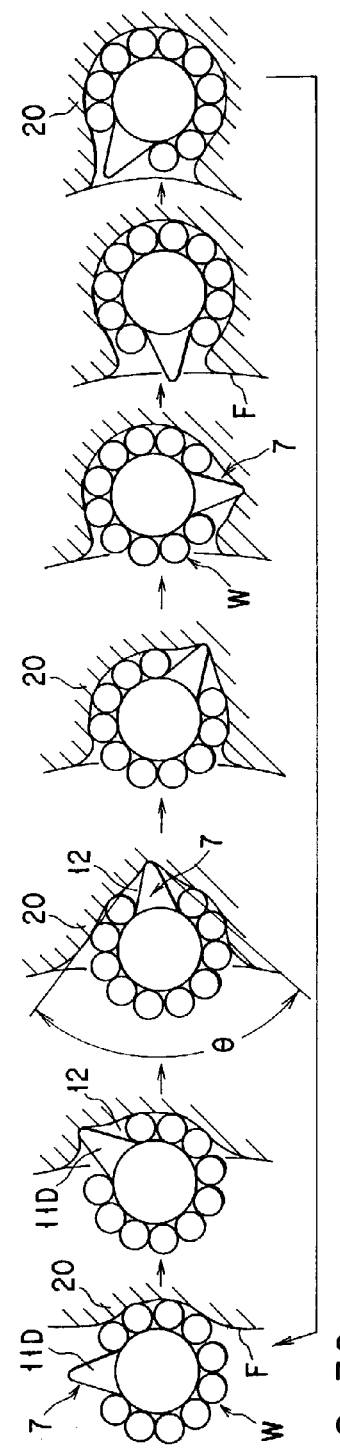
Figure 5A:
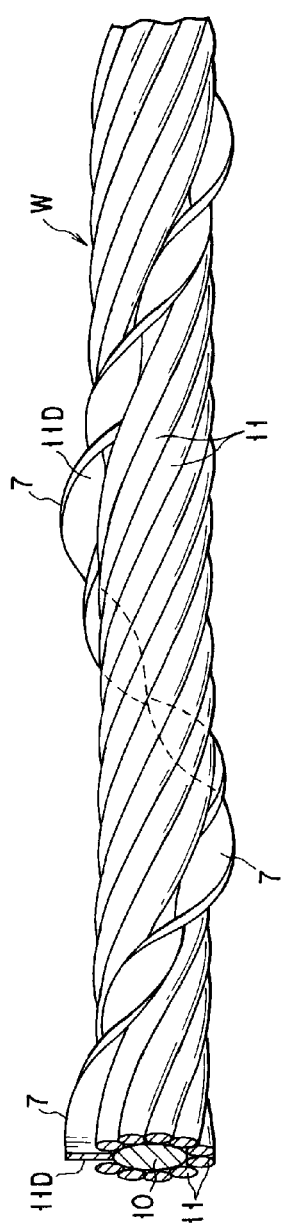
FIGS. 5A to 5C show the wire rope of the treatment portion of the treatment device for the endoscope according to another embodiment of the first aspect of the present invention.
Figure 5B:
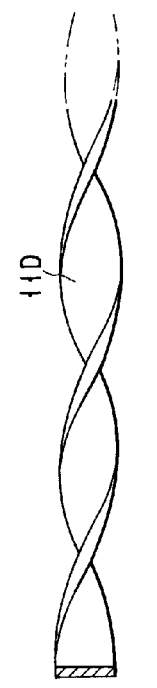

On the other hand, for the embodiment shown in FIGS. 3A to 3C, in the structure in which the spiral convex portion 7 is disposed similarly as the embodiment shown in FIGS. 1A to 1D, one of the plurality of side strand wires 11 is a triangular side strand wire 11D having a triangular sectional shape, and an upper half portion of the triangular side strand wire 11D in a wound state around the core strand wire 10 projects from the outer periphery of the wire rope W formed by the other side strand wires 11 to form the spiral convex portion 7.

In the embodiment shown in FIGS. 3A to 3C, the spiral convex portion 7 is formed in a knife edge shape, and large voids as the drain ditches 12 of the viscous material of the surface F are disposed on the opposite sides of the portion. Therefore, as compared with the embodiment shown in FIGS. 1A to 1D, the bite type tool function, fixing engagement function, and removal action of the viscous material are enhanced and the capturing/fastening capability of the living tissue 20 is further enhanced.

One embodiment of a treatment device for an endoscope 1B according to a second aspect of the present invention will next be described with reference to FIGS. 4A to 4D. That is, in the treatment portion 6 including the wire rope W formed by winding a plurality of side strand wires 11 around the core strand wire 10, for the wire rope 6 of this embodiment, two of six side strand wires 11 are omitted, and this omitted portion is formed as a broad spiral concave portion 8. Moreover, the space of the spiral concave portion 8 is used to continuously dispose a wave-form portion 9 having a circular arc shape in one side strand wire 11E and the portion is allowed to project inside the loop 5 at required intervals in the structure. This wave-form portion 9 functions as the bite type tool portion or fixing engagement tool portion in capturing/fastening the living tissue 20.

In the above-described embodiment shown in FIGS. 4A to 4D (see FIG. 4D), the vertex of the wave-form portion 9 disposed opposite to the surface F of the living tissue 20 is first bonded to capture and fasten the living tissue 20, and bites into the tissue to fixedly engage with the tissue, so that the capturing/fastening of the tissue can accurately and easily be performed. Moreover, the wire rope can be retracted and stored in the main tube 2 in a mode in which the wave-form portions 9 do not interfere with each other (the wave-form portion 9 of the folded/superimposed wire rope W is positioned in the straight outer periphery on a counterpart side). Therefore, the wire rope is smoothly accommodated without damaging the wire rope W or main tube 2. Furthermore, only the side strand wire 11E can form the wave-form portion 9, and therefore it is easy to form the treatment portion 6 as compared with the structure in which the engagement needle having the conventional structure is attached later. It is to be noted that for the wave-form portion 9 disposed inside the loop 5, the wave-form portion 9 is sometimes disposed only in a front half portion of the loop 5 as not shown.

Another embodiment of the treatment device for the endoscope according to the present invention will next be described with reference to FIGS. 5A to 5C and 6A to 6C. First, in another embodiment of the first aspect of the present invention shown in FIGS. 5A to 5C, the side strand wire 11D in the embodiment shown in FIGS. 3A to 3C includes a twist drill mode obtained by twisting a wire material having a rectangular sectional surface centering on a wire material axial center, and the side strand wire 11D forms the spiral convex portion 7. In the embodiment shown in FIGS. 5A to 5C, a ditch of the spiral portion existing in the twist drill mode remarkably effectively functions as the above-described drain ditch of the viscous material, and therefore the above-described peculiar action based on the drain ditch action further becomes remarkable. Moreover, the side strand wire 11D can easily be wound around the core strand wire 10.

Figure 6A:
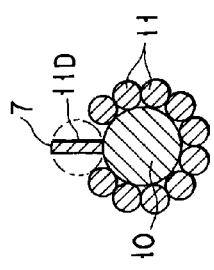
FIGS. 6A to 6C show another mode of the wire rope of the treatment portion of the treatment device for the endoscope according to the present invention.
Figure 5C:
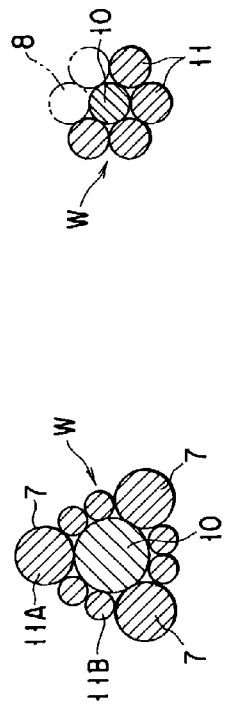
Figure 6B:
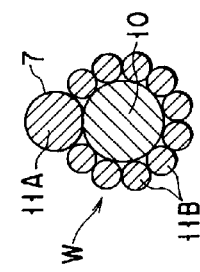
Figure 6C:
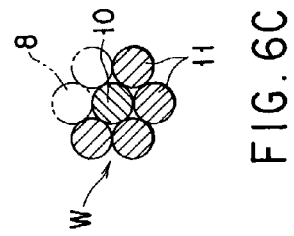

On the other hand, in the embodiment shown in FIGS. 6A to 6C in which the spiral convex portion 7 and spiral concave portion 8 are disposed similarly as the embodiment shown in FIGS. 1A to 1D and 2A to 2C, a mode in FIGS. 6A, 6B uses one or three large-diameter side strand wires 11A to form a single or three spiral convex portions 7 which appear on the outer periphery of the wire rope W. Moreover, a mode shown in FIG. 6C includes the wire rope W including the spiral concave portion 8 by the omission of the side strand wire 11 in the embodiment shown in FIGS. 2A to 2C, and two side strand wires 11 disposed adjacent to each other are omitted to form the spiral concave portion 8 as a broad ditch. In the embodiment of FIG. 6C, the action of the spiral concave portion 8 in the embodiment shown in FIGS. 2A to 2C becomes further remarkable.

Figure 7A:
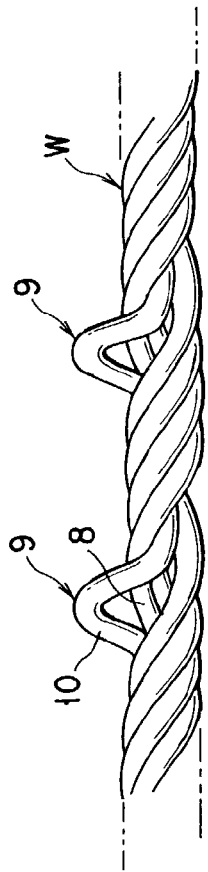
FIGS. 7A to 7C show the wire rope according to another embodiment of the treatment device for the endoscope of the second aspect of the present invention.
Figure 7B:
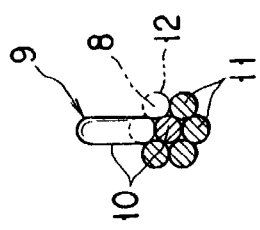
Figure 7C:
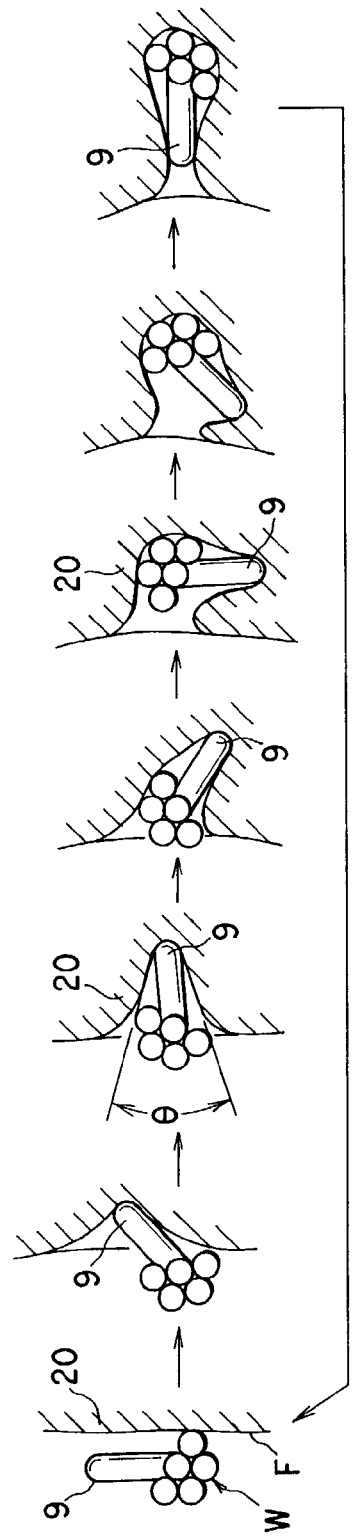

Another embodiment of the treatment device for the endoscope according to the second aspect of the present invention will next be described with reference to FIGS. 7A to 7C. That is, in the embodiment shown in FIGS. 7A to 7C, the wave-form portion 9 is disposed similarly as the embodiment shown in FIGS. 4A to 4D, two side strand wires disposed adjacent to each other are omitted from six side strand wires 11 to form the broad spiral concave portion 8, and the space of the spiral concave portion 8 is used to extend the core wire 10 and to raise the wave-form portion 9 above the outer periphery of the wire rope. Also in the embodiment shown in FIGS. 7A to 7C, the spiral concave portion 8 as the broad ditch effectively functions as the drain ditch 12 which has a large discharge capacity. Moreover, a group of wave-form portions 9 is allowed to project only inside the loop 5, and the above-described capturing/fastening properties and containing property into the main tube 2 can further be enhanced.

Figure 8A:
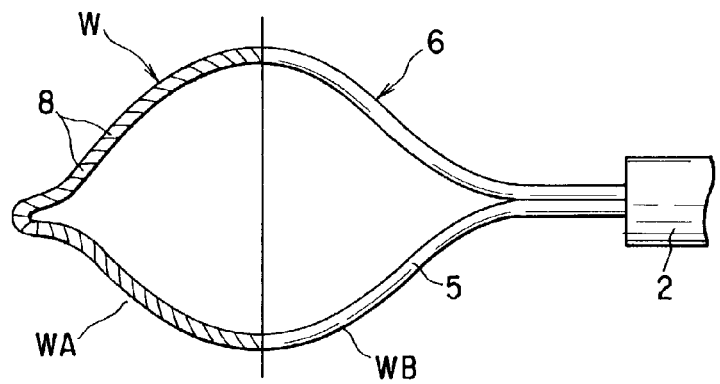
FIGS. 8A to 8C show another mode of the treatment device for the endoscope according to the present invention.
Figure 8B:
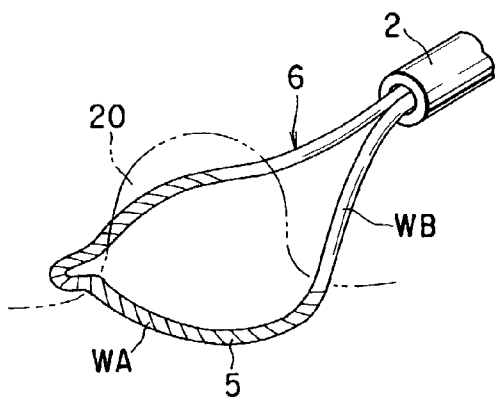
Figure 8C:
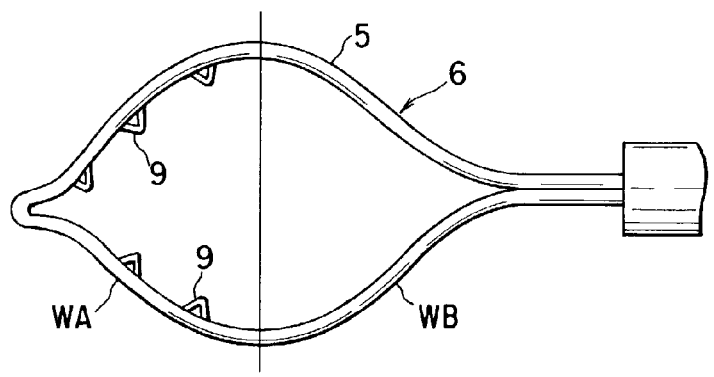

On the other hand, the embodiment shown in FIGS. 8A to 8C corresponds to an application example of the first aspect of the present invention in which the wire rope W including the spiral concave portion 8 by the omission of the side strand wire 11 on the outer periphery forms the loop for treatment 5. The front half portion of the loop 5 of the treatment portion 6 of this embodiment forms a wire rope WA including the spiral concave portion 8 by the omission of some of the side strand wires 11 shown in FIGS. 2A to 2C and 6C. A wire rope WB as a rear half portion of the loop 5 forms a rigid wire rope (having a rigidity higher than that of WA) in which any side strand wire 11 is not omitted and the spiral concave portion 8 is not disposed. The ropes WA and WB constitute the loop 5 as the single seamless wire rope W.

In the treatment portion 6 including the loop 5 of FIG. 8A (see FIG. 8B), the soft WA and rigid WB are formed in a buckling mode in a boundary point, and the living tissue 20 of the convex portion, such as the polyp, can be captured so that a capture operation by the loop 5 is further facilitated. It is to be noted that in the structure including the soft mode of the front half portion/rigid mode of the rear half portion of the loop 5, the wave-form portion 9 may also be disposed in the front half portion (FIG. 8C). Alternatively, in a two-layered side strand wire mode obtained by winding another wire material around the wire rope W of the rear half portion, soft/rigid means for obtaining rigidity higher than that of the front half portion of a single-layer side strand wire mode may also be used.

Another embodiment of the treatment device for the endoscope according to the present invention will next be described with reference to FIGS. 9 and 10A to 10C. Moreover, in the embodiment shown in FIG. 9, the wire rope W is constituted by intertwining two large-diameter strand wires 21, and similarly two small-diameter strand wires 22. For the size, a large-diameter strand diameter=0.25 mm, small-diameter strand diameter=0.125 mm, and a maximum diameter of the wire rope W is 0.5 mm. Similarly as the embodiment of FIG. 1, the fastening mode is obtained in which the large-diameter strand wire 21 of the spiral convex portion is slid/dislocated with respect to the surface F and successively bites into the living tissue 20. Moreover, mainly the small-diameter strand wire 22 functions as the drain ditch of the viscous material of the living tissue surface, and functions as the bite type tool portion or fixing engagement portion, so that the effective capturing/fastening of the living tissue by the loop for treatment is possible.

Figure 9:
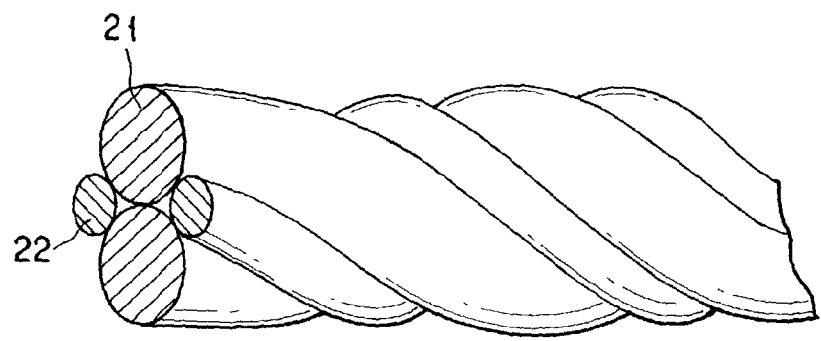
FIG. 9 shows another mode of the treatment device for the endoscope according to the present invention, and is a front view of the wire rope of the loop for treatment.
Figure 10A:
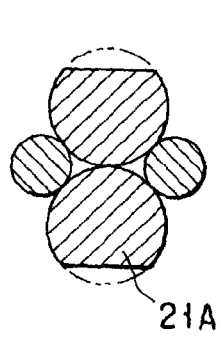
FIGS. 10A to 10C show another mode of the treatment device for the endoscope according to the present invention.
Figure 10B:
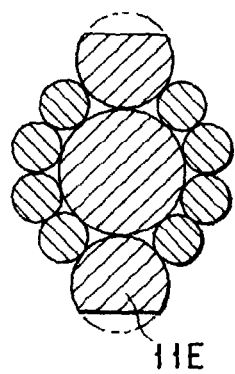
Figure 10C:
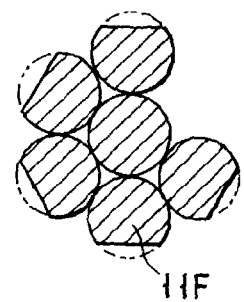

On the other hand, for the embodiment shown in FIG. 10, in the respective embodiments shown in FIGS. 1, 2, 9, the wire rope is subjected to a diameter reduction wire drawing processing using a die, and an edge-shaped end surface is continuously formed in a part of each strand wire in a wire rope axial line direction in the structure.

Concretely, in the embodiment shown in FIG. 1, with respect to the maximum diameter of the wire rope=0.5 mm, the die inner diameter=0.45 mm is used, and the wire rope is passed through the die and subjected to the diameter reduction wire drawing processing. In this case, after a swaging processing, the diameter reduction wire drawing processing may be performed by a die drawing processing. Thereby, when the spiral strand wire 21A, 11E, or 11F having a continuous edge-shaped end surface bites into the living tissue, the living tissue can more firmly be captured or fastened by the structure of the edge-shaped end surface.

It is to be noted that the treatment device for the endoscope of the present invention is not limited to the above-described embodiments, and can also be applied to a loop structure of a retaining snare to temporarily bond the polyp, and a rope wire of a recovery basket or crushed stone basket for extracting a stone formed in an inner cavity or removed polyp.

As described above, the treatment device for the endoscope of the present invention has a superior capability of accurately and remarkably easily capturing/fastening the living tissue with respect to an affected area such as the polyp, and has a satisfactory containment capacity of the loop for treatment into the main tube. Additionally, the device is easily formed/processed, can be provided at a low cost, and effectively enhances a medical treatment capability and convenience.

As described above in detail, according to the present invention, in a treatment device for an endoscope, comprising: a treatment portion in which an operation wire is forward/backward moveably inserted into a main tube of an elongated flexible tube to be inserted in a body, a tip end of the operation wire forms a loop for treatment by itself in a projection state from the main tube, and the loop is adapted to be retractable and storable in the main tube, the treatment portion is formed by a wire rope obtained by integrally intertwining a plurality of side strand wires around a core strand wire. Moreover, spiral convex or concave portions continuously disposed along the outer periphery of the wire rope are formed with the side strand wires.

Moreover, according to the present invention, in the treatment device for the endoscope, comprising: the treatment portion in which the operation wire is forward/backward moveably inserted into the main tube of the elongated flexible tube to be inserted in the body, the tip end of the operation wire forms the loop for treatment by itself in the projection state from the main tube, and the loop is adapted to be retractable and storable in the main tube, the treatment portion includes the wire rope formed by winding the side strand wires around the core strand wire. Moreover, the core strand wire or side strand wire forms a wave-form portion which projects from the outer periphery of the wire rope and has a circular arc shape and the wave-form portions are continuously disposed in a longitudinal direction of the wire rope.

Furthermore, according to the present invention, in the treatment device for the endoscope, comprising: the treatment portion in which the operation wire is forward/backward moveably inserted into the main tube of the elongated flexible tube to be inserted in the body, the tip end of the operation wire forms the loop for treatment by itself in the projection state from the main tube, and the loop is adapted to be retractable and storable in the main tube, the treatment portion is formed by the wire rope obtained by integrally intertwining at least two strand wires having different outer diameters. Moreover, the spiral convex and concave portions continuously disposed along the outer periphery of the wire rope are formed by the strand wires.

By the constitution, there is provided a superior capability of accurately and remarkably easily capturing/fastening a living tissue with respect to an affected area such as a polyp, the containment capacity of the loop for treatment into the main tube is satisfactory, further the device can easily be formed/processed and provided at a low cost, and further enhancement of the medical treatment property and enhancement of convenience can be achieved.

What is claimed is:

1. A treatment device for an endoscope, comprising a treatment portion in which an operation wire is forward/backward moveably inserted into a main tube of an elongated flexible tube to be inserted into a body, a tip end of the operation wire forms a loop for treatment by itself in a projection state from the main tube, and the loop is adapted to be retractable and storable in the main tube;
wherein the treatment portion is formed with a wire rope comprising a single internal core strand wire having a substantially circular section and a plurality of side strand wires integrally formed on an outer periphery of the core strand wire and each having a substantially circular section,
at least one side strand wire of the plurality of side strand wires is provided with a diameter larger than the other side strand wires so as to form a spiral convex portion continuous along the wire rope in a longitudinal direction, the sections of the other side strand wires each having a same diameter and together constitute a substantially circular section coaxial with the core strand wire having the substantially circular section, and a center of the at least one side strand wire which forms the spiral convex portion is located substantially on an outer circumference of a section of the substantial circular shape formed by the other side strand wires.

2. The treatment device for an endoscope according to claim 1, wherein a relationship of Y>X≧1 is satisfied when a number of the at least one side strand wire having the larger diameter is X and a number of the other side strand wires is Y, wherein 1 is a number of the core strand wire.

3. The treatment device for an endoscope according to claim 1, wherein a relationship of A≧B>C is satisfied when an external diameter of the core strand wire is A, an external diameter of the at least one side strand wire having the larger diameter is B, and an external diameter of the other side strand wires is C.

4. A treatment device for an endoscope, comprising a treatment portion in which an operation wire is forward/backward moveably inserted into a main tube of an elongated flexible tube to be inserted into a body, a tip end of the operation wire forms a loop for treatment by itself in a projection state from the main tube, and the loop is adapted to be retractable and storable in the main tube;
wherein the treatment portion is formed with a wire rope comprising a single internal core strand wire having a substantially circular section and a plurality of side strand wires integrally formed on an outer periphery of the core strand wire and each having a substantially circular section,
at least one side strand wire of the plurality of side strand wires is provided with a diameter larger than the other side strand wires so as to form a spiral convex portion continuous along the wire rope in a longitudinal direction, the sections of the other side strand wires each have the same diameter, thereby the other side strand wires being arranged to be in contact with a circumscribed circle coaxial with the core strand wire having a substantially circular section, and a center of the at least one side strand wire which forms the spiral convex portion is located substantially on the circumscribed circle.

5. A treatment device for an endoscope, comprising a treatment portion in which an operation wire is forward/backward moveably inserted into a main tube of an elongated flexible tube to be inserted into a body, a tip end of the operation wire forms a loop for treatment by itself in a projection state from the main tube, and the loop is adapted to be retractable and storable in the main tube;
wherein the treatment portion is formed with a wire rope comprising a single internal core strand wire having a substantially circular section and a plurality of side strand wires integrally formed on an outer periphery of the core strand wire and each having a substantially circular section,
at least one side strand wire of the plurality of side strand wires is provided with a diameter larger than the other side strand wires so as to form a spiral convex portion continuous along the wire rope in a longitudinal direction, and the plurality of side strand wires comprise two types of element wires, the at least one side strand wire has an outer diameter substantially twice as large as an outer diameter of that of the other side strand wires.

* * * * *